(12) United States Patent
Desmurs et al.

(10) Patent No.: US 8,703,107 B2
(45) Date of Patent: Apr. 22, 2014

(54) COSMETIC COMPOSITION INCLUDING LEUCODOPACHROME DERIVATIVE

(75) Inventors: Jean-Roger Desmurs, Cannes (FR); Sabine Delaire, Rueil Malmaison (FR)

(73) Assignee: Chanel Parfums Beaute, Neuilly sur Seine (FR)

( * ) Notice: Subject to any disclaimer, the term of this patent is extended or adjusted under 35 U.S.C. 154(b) by 0 days.

(21) Appl. No.: 13/496,654

(22) PCT Filed: Sep. 6, 2010

(86) PCT No.: PCT/FR2010/051845
§ 371 (c)(1),
(2), (4) Date: Mar. 16, 2012

(87) PCT Pub. No.: WO2011/033207
PCT Pub. Date: Mar. 24, 2011

(65) Prior Publication Data
US 2012/0177588 A1    Jul. 12, 2012

(30) Foreign Application Priority Data
Sep. 16, 2009    (FR) ..................................... 09 56365

(51) Int. Cl.
*A61K 8/49*  (2006.01)
*A61Q 19/02* (2006.01)
*C07D 209/42* (2006.01)

(52) U.S. Cl.
USPC ............................. 424/62; 514/419; 548/492

(58) Field of Classification Search
None
See application file for complete search history.

(56) References Cited

U.S. PATENT DOCUMENTS 3,780,062 A      12/1973  Kaiser et al.
5,399,713 A  *   3/1995   Knuebel et al. ............... 548/490
5,932,608 A      8/1999   Nguyen et al.

FOREIGN PATENT DOCUMENTS

EP           1254650 B1  *  7/2007

* cited by examiner

*Primary Examiner* — Robert A Wax
*Assistant Examiner* — Randeep Singh
(74) *Attorney, Agent, or Firm* — Young & Thompson

(57) ABSTRACT

A cosmetic or dermatological composition contains, in a physiologically acceptable medium, at least one compound from Formula (I). A method of using the composition, for reducing or preventing pigmenting, and/or whitening and/or lightening of the skin is described, as well as novel compounds from Formula (I') that are included in Formula (I).

13 Claims, No Drawings

COSMETIC COMPOSITION INCLUDING LEUCODOPACHROME DERIVATIVE

The present invention relates to a cosmetic composition comprising a derivative of leucodopachrome, and also to the use thereof as skin-depigmenting agent. The invention also relates to a process for depigmenting the skin using said composition.

Human skin color depends on various factors, and in particular on the seasons of the year, on race and on sex. It is mainly determined by the nature and the concentration of melanin produced by melanocytes. Melanocytes are specialized cells which synthesize melanin by means of specific organelles, melanosomes. In addition, at various times in their life, certain individuals experience the appearance of darker and/or more colored spots on the skin and more especially on the hands, which give the skin a heterogeneity. These spots are also due to a high concentration of melanin in the keratinocytes located at the skin surface.

The use of harmless topical depigmenting substances that are very effective is most particularly desired with a view to treating regional hyperpigmentations due to melanocyte hyperactivity, such as idiopathic melasmas, occurring during pregnancy ("mask of pregnancy" or chloasma) or oestro-progestin contraception, localized hyperpigmentations due to benign melanocyte hyperactivity and proliferation, such as senile pigmentation spots referred to as actinic lentigo, accidental hyperpigmentations, possibly due to post-lesional cicatrization or photosensitization, and also certain forms of leukoderma, such as vitiligo. For the latter (the cicatrizations possibly resulting in a scar that gives the skin a whiter appearance), since it is not possible to repigment the lesioned skin, the areas of residual normal skin are depigmented so as to give the skin as a whole a homogeneous white tint.

The mechanism of formation of skin pigmentation, i.e. of the formation of melanin, is particularly complex and involves, schematically, two possible pathways for eumelanin:

Dopaquinone→leucodopachrome→dopachrome→DHI (5,6-dihydroxyindole or DHI)→indole-5,6-quinone
Dopaquinone→leucodopachrome→dopachrome→DHICA (5,6-dihydroxyindole-2-carboxylic acid)

Tyrosinase (monophenol oxygenase EC 1.14.18.1: oxygen oxidoreductase EC 1.14.18.1) is the essential enzyme involved in this series of reactions. It catalyzes in particular the reaction for conversion of tyrosine to Dopa (dihydroxyphenylalanine) by virtue of its hydroxylase activity and the reaction for conversion of Dopa to dopaquinone by virtue of its oxidase activity. This tyrosinase acts only when it is in the maturation state under the action of certain biological factors.

A substance is recognized as being a depigmenting or anti-pigmenting substance if it acts directly on the vitality of epidermal melanocytes where melanogenesis takes place, and/or if it interferes with one of the steps of melanin biosynthesis, either by inhibiting one of the enzymes involved in melanogenesis, or by being inserted as a structural analog of one of the chemical compounds of the melanin synthesis chain, which chain can then be blocked, and thus ensure depigmentation.

The cosmetic substances most commonly used as depigmenting substances are, more particularly, ascorbic acid and its derivatives, including ascorbyl glucoside, and also certain plant extracts (especially liquorice extracts).

There remains the need, however, for a new agent for bleaching human skin which is very effective and which is well tolerated.

In this regard, the applicant has, surprisingly and unexpectedly, discovered that certain leucodopachrome derivatives exhibit a good depigmenting activity. The leucodopachrome derivatives are known compounds that are involved in particular in the synthesis of melanin. Unexpectedly, the inventors have shown that certain leucodopachrome derivatives, although being precursors of melanin, exhibit bleaching properties.

More specifically, one subject of the invention is therefore, according to a first aspect, a cosmetic or dermatological composition, characterized in that it contains, in a physiologically acceptable medium, at least one compound of formula (I)

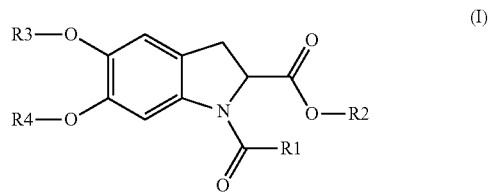

where R1 is
   a hydrogen, or
   a saturated or unsaturated, linear or branched C1-C18 alkyl, optionally substituted with one or more aryl groups, or
   an aryl optionally substituted with one or more hydroxyl and/or acyloxy groups;
R2 is:
   a hydrogen, or
   a saturated or unsaturated, linear or branched C1-C18 alkyl, or
   an aryl that is optionally substituted, in particular with acyloxy groups, or
   a polyethylene glycol (PEG) chain or a polyethylene glycol monoalkyl ether chain;
R3 and R4 are, independently of one another:
   a hydrogen, or
   an acyl group of formula R5-CO— where R5 is a saturated or unsaturated, linear or branched C1-C18 alkyl, optionally substituted with one or more aryl groups that are optionally substituted, in particular with acyloxy groups, or
   an aryl that is optionally substituted, in particular with acyloxy groups.

The compounds of formula (I) include the enantiomers of these compounds and mixtures thereof in all proportions. The (S) enantiomer is preferred for use in the present invention.

Another subject of the invention is, according to a second aspect, a process for reducing or preventing pigmentation and/or bleaching and/or lightening the skin, comprising the application to the skin of a cosmetic or dermatological composition, characterized in that it contains, in a physiologically acceptable medium, at least one compound of formula (I) as described previously.

According to a third aspect, one subject of the present invention is the use of a compound of formula (I) as described previously as a depigmenting and/or anti-pigmenting and/or bleaching and/or lightening agent.

According to a fourth aspect, one subject of the invention is a compound of formula (I')

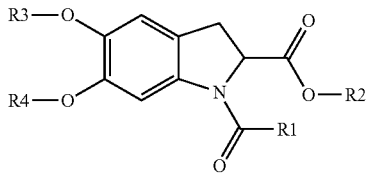

(I')

where R1 is
- a saturated or unsaturated, linear or branched C1-C18 alkyl, optionally substituted with one or more aryl groups, or
- an aryl optionally substituted with one or more hydroxyl and/or acyloxy groups;

R2 is:
- a saturated or unsaturated, linear or branched C3-C18 alkyl, or
- an aryl that is optionally substituted, in particular with acyloxy groups, or
- a polyethylene glycol (PEG) chain or a polyethylene glycol monoalkyl ether chain;

R3 and R4 are, independently of one another:
- an acyl group of formula R5-CO— where R5 is a saturated or unsaturated, linear or branched C1-C18 alkyl, optionally substituted with one or more aryl groups that are optionally substituted, in particular with acyloxy groups, or
- an aryl that is optionally substituted, in particular with acyloxy groups.

Compounds of Formula (I) and (I')

The compounds of formula (I) and (I') according to the invention make it possible to effectively depigment and/or lighten the skin of human beings. They are especially intended to be applied to the skin of individuals who have brownish pigmentation spots, senescence spots, or to the skin of individuals who desire to combat the appearance of a brownish color originating from melanogenesis, for example following exposure to ultraviolet radiation.

For the compounds of formula (I):

R1 denotes:
- a hydrogen, or
- a saturated or unsaturated, linear or branched C1-C18 alkyl, optionally substituted with one or more aryl groups, or
- an aryl optionally substituted with one or more hydroxyl and/or acyloxy groups;

R2 denotes:
- a hydrogen, or
- a saturated or unsaturated, linear or branched C1-C18 alkyl, or
- an aryl that is optionally substituted, in particular with acyloxy groups, or
- a polyethylene glycol (PEG) chain or a polyethylene glycol monoalkyl ether chain;

R3 and R4 are, independently of one another:
- a hydrogen, or
- an acyl group of formula R5-CO— where R5 is a saturated or unsaturated, linear or branched C1-C18 alkyl, optionally substituted with one or more aryl groups that are optionally substituted, in particular with acyloxy groups, or
- an aryl that is optionally substituted, in particular with acyloxy groups.

According to one particular embodiment, the compound (I) is in the form of a dimer, the monomers of which may be bonded covalently via a single bond or by means of at least one atom such as a heteroatom to the radical R1 or R2:

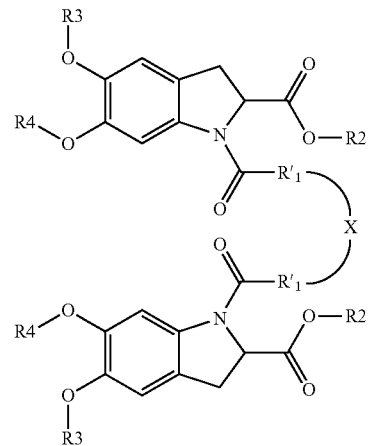

As nonlimiting examples of the compound (I) according to the invention, mention may especially be made of:
- the dimethyl [S—(R*,R*)]-1,1'-[thiobis(1-oxo-3,1-propanediyl)]bis[5,6-bis(acetyloxy)-2,3-dihydro-1H-indole-2-carboxylate of formula

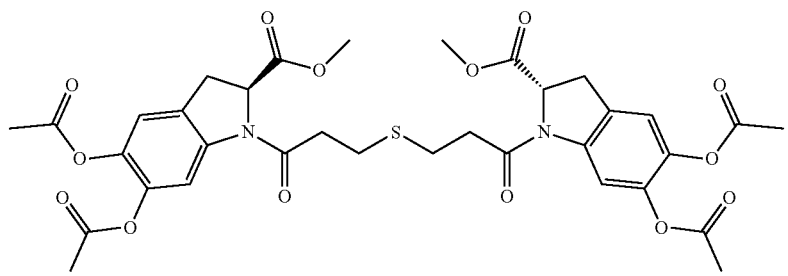 [SMILES: COC(=O)[C@@H]1Cc2cc(OC(C)=O)c(OC(C)=O)cc2N1C(=O)CCSCCC(=O)N1c2cc(OC(C)=O)c(OC(C)=O)cc2C[C@H]1C(=O)OC]

the 2,2-dimethyl-1-oxopropoxy)methyl (S)-5,6-bis(acetyloxy)-1-[3-(acetylthio)-1-oxopropyl]-2,3-dihydro-1H-indole-2-carboxylate of formula

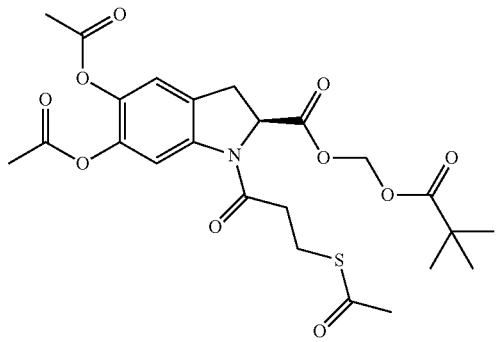 [SMILES: CC(=O)Oc1cc2c(cc1OC(C)=O)N(C(=O)CCSC(C)=O)[C@H](C(=O)OCOC(=O)C(C)(C)C)C2]

the methyl [S—(R*,R*)]-5,6-bis(acetyloxy)-1-[3-(acetylthio)-2-methyl-1-oxopropyl]-2,3-dihydro-1H-indole-2-carboxylate of formula

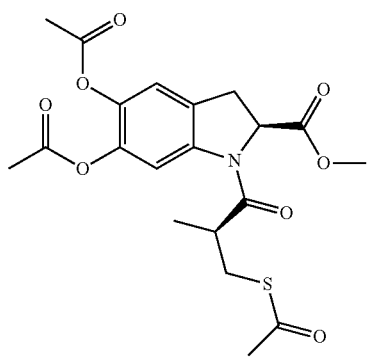 [SMILES: COC(=O)[C@@H]1Cc2cc(OC(C)=O)c(OC(C)=O)cc2N1C(=O)[C@H](C)CSC(C)=O]

the methyl (S)-5,6-bis(acetyloxy)-2,3-dihydro-1-[1-oxo-3-[(phenylmethyl)thio]propyl]-1H-indole-2-carboxylate of formula

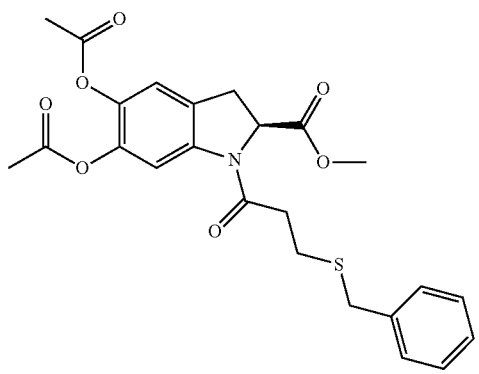 [SMILES: COC(=O)[C@@H]1Cc2cc(OC(C)=O)c(OC(C)=O)cc2N1C(=O)CCSCc1ccccc1]

the methyl (S)-5,6-bis(acetyloxy)-1-[3-(benzoylthio)-1-oxopropyl]-2,3-dihydro-1H-indole-2-carboxylate of formula

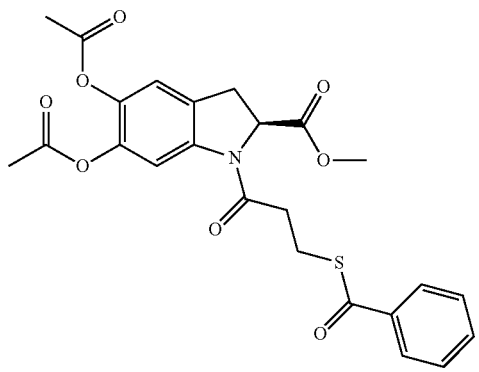 [SMILES: COC(=O)[C@@H]1Cc2cc(OC(C)=O)c(OC(C)=O)cc2N1C(=O)CCSC(=O)c1ccccc1]

the ethyl ester of triacetyl leucodopachrome of formula

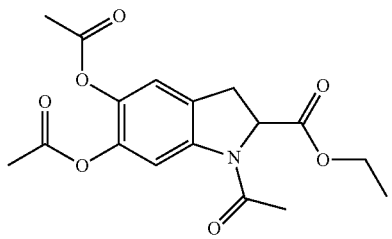 [SMILES: CCOC(=O)C1Cc2cc(OC(C)=O)c(OC(C)=O)cc2N1C(C)=O]

the methyl ester of triacetyl leucodopachrome of formula

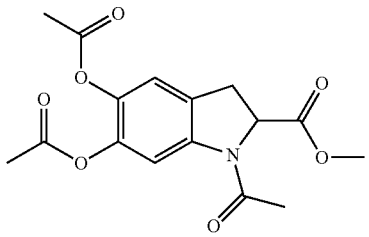 [SMILES: COC(=O)C1Cc2cc(OC(C)=O)c(OC(C)=O)cc2N1C(C)=O]

Preferably, for the compounds of formula (I) and (I'), R1 denotes:
  a saturated or unsaturated, linear or branched, C1-C18 alkyl optionally substituted with one or more aryl groups, or
  an aryl optionally substituted with one or more hydroxyl and/or acyloxy groups.

Preferably, R1 denotes a linear C1-C18 alkyl, and more preferably still R1 is $CH_3$.

For the compounds of formula (I) and (I'), preferably R2 denotes:
  an aryl that is optionally substituted, in particular with acyloxy groups,
  a polyethylene glycol (PEG) chain or a polyethylene glycol monoalkyl ether chain.

More preferably, R2 denotes a polyethylene glycol (PEG) chain. Indeed, the applicant has observed that when R2 is a polyethylene glycol (PEG) chain, the solubility of the compound (I) or (I') in water is improved. As a result, the compound (I) or (I') can then be introduced more easily into cosmetic compositions comprising an aqueous phase.

As a variant, in the formula (I), R2 denotes a linear C1-C18 alkyl, and more preferably, R2 is —$CH_3$ or —$CH_2$—$CH_3$.

Moreover, in the formula (I'), R2 may advantageously denote a linear C3-C18 alkyl group and more preferably an n-propyl group.

According to one particularly preferred embodiment, for the compounds of formula (I) according to the invention, R1 denotes —CH$_3$, and R2 denotes —CH$_3$ or —CH$_2$—CH$_3$.

Preferably, in the formula (I) or (I'), R3 and R4 are, independently of one another:
- an acyl group of formula R5-CO— where R5 is a saturated or unsaturated, linear or branched C1-C18 alkyl, optionally substituted with one or more aryl groups that are optionally substituted, in particular with acyloxy groups, or
- an aryl that is optionally substituted, in particular with acyloxy groups.

According to one particularly preferred embodiment, for the compounds of formula (I) according to the invention, R3 and R4 are both CH$_3$—CO— acetyl groups.

According to one preferred embodiment, the compound of formula (I) according to the invention is the methyl ester of triacetyl leucodopachrome (II) or the ethyl ester of triacetyl leucodopachrome (III):

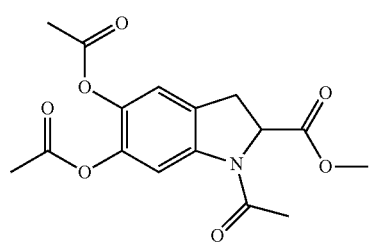

(II)

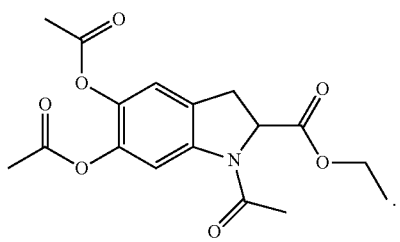

(III)

In particular, the composition according to the invention comprises one of the enantiomers or a racemic (50/50) mixture of two optically active compounds of formula (I). More preferably, the compound of formula (I) according to the invention is the methyl ester of (S) triacetyl leucodopachrome or the ethyl ester of (S) triacetyl leucodopachrome.

Moreover, a preferred example of the compound of formula (I') is the propyl ester of triacetyl leucodopachrome of formula (IV):

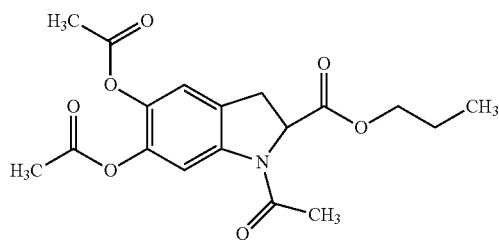

(IV)

which may especially be present in the form of one of its enantiomers or a racemic (50/50) mixture of two optically active compounds of formula (IV).

The compound of formula (I) may especially be present in the composition according to the invention in an amount ranging from 0.00001 to 10% by weight and preferably from 0.001 to 5% by weight relative to the total weight of the composition.

The compounds of formula (I) may be obtained by processes described in the prior art. Mention may be made, by way of example, of the publications of Wyler H., Chiovini J., *Helvetica Chimica Acta,* 1968, 51, 1476-1494; of Woelcke Uwe; Kaiser Ado; Koch Wolfgang; Scheer Marcel, *Helvetica Chimica Acta,* 1970, 53(7), 1704-1708; of Wyler H., Dreiding Andre S., *Helvetica Chimica Acta,* 1962, 45, 638-640; of Mabry T. J.; Wyler H.; Sassu C.; Mercier M.; Parikh I.; Dreiding Andre S., *Helvetica Chimica Acta,* 1962, 45, 640-647; of Berestovitskaya V. M.; Perekalin V. V.; Sopova A. S.; *Zhurnal Obshchei Khimii,* 1966, 2(6), 1123-1124; of Omote Yoshimori; Fujinuma Yoshimori; Kuo Kung-Tu; Sugiyama Noboru, *Nippon Kagaku Zasshi,* 1966, 87(7), 760-762, or of Davies Roger; Laird William M.; Synge Richard L. M.; *Phytochemistry,* 1975, 14(7), 1591-1596.

By way of illustration and nonlimitingly, the compound (II) may be obtained from 3,4-dihyroxy-(L)-phenylalanine, hereinafter referred to as (L)-Dopa (V).

The product S-(L)-Dopa methyl ester or methyl ester of (L)-Dopa, referred to as product (VI) is obtained by esterification of the product (L)-Dopa (V), then undergoes an oxidation, then a reduction in order to obtain, after acid treatment, the methyl ester of (S)-5,6-dihydroxyindoline-2-carboxylic acid ((L)-cyclodopa methyl ester or (L)-leucodopachrome methyl ester, product (VII)).

Alternatively, and still nonlimitingly, the compound of formula (II) may be obtained from betanin, a natural molecule extracted from red beet, according to the following method of synthesis:

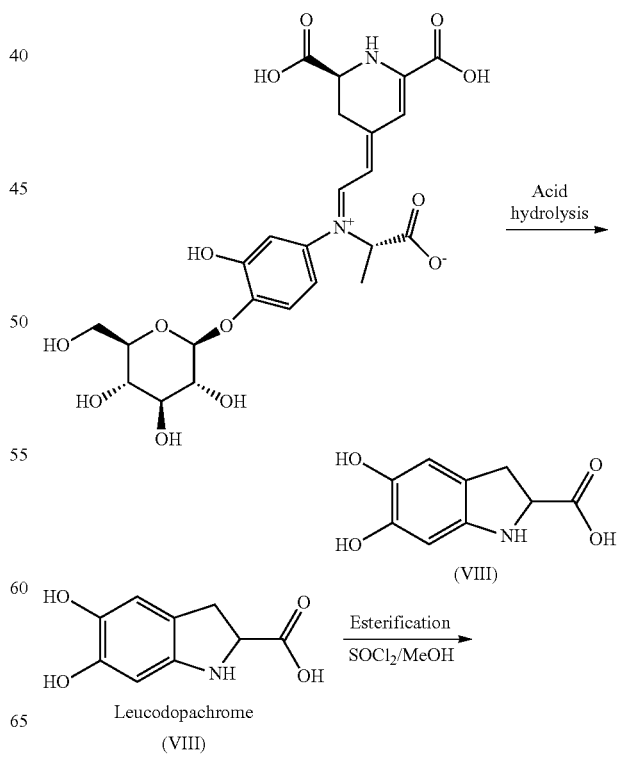

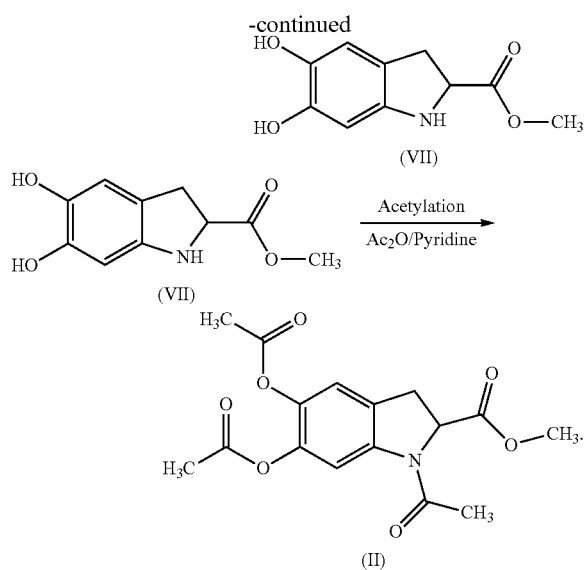

The esterification and acetylation steps that make it possible to synthesize the methyl ester of triacetyl leucodopachrome (compound of formula (II)) from leucodopachrome (VIII) may be analogous to those of the process described previously.

Besides the compound of formula (I) described previously, the composition according to the invention may also comprise at least one customary additive in the cosmetic field, such as for example at least one compound chosen from an emollient or humectant, a gelling and/or thickening agent, a surfactant, an oil, a wax, a silicone elastomer, a sunscreen, a dye, an organic or inorganic filler, a preserving agent, an antioxidant, an active agent, a sequestrant and a fragrance.

In particular, the composition according to the invention may contain, nonlimitingly, one or more of the following additives:

One or more agents for gelling and/or thickening the aqueous phase, chosen for example from hydrophilic or amphiphilic, crosslinked or uncrosslinked homopolymers and copolymers of acryloylmethylpropanesulfonic acid (AMPS) and/or of acrylamide and/or of acrylic acid and/or of salts or esters of acrylic acid such as ammonium acryloyldimethyltaurate/VP copolymer and ammonium acryloyldimethyltaurate/beheneth-25 methacrylate copolymer, especially those sold under the names Aristoflex AVC and HMB from Clariant, cellulose derivatives, gums of plant origin (guar, carob, alginates, carrageenans, pectin) or of microbial origin (xanthan), clays (laponite).

Said gelling and/or thickening agent may be present in the composition in an amount of the order of 0.01 to 5% by weight, relative to the total weight of the composition;

One or more surfactants, preferably emulsifiers, whether they are nonionic, anionic, cationic or amphoteric, and in particular the fatty acid esters of polyols such as glycerol fatty acid esters, sorbitan fatty acid esters, polyethylene glycol fatty acid esters and sucrose fatty acid esters; polyethylene glycol fatty alcohol ethers; alkyl polyglucosides; polyether-modified polysiloxanes; betaine and derivatives thereof; polyquaterniums; sulfate salts of ethoxylated fatty alcohols; sulfosuccinates; sarcosinates; alkyl and dialkyl phosphates and salts thereof; and fatty acid soaps. Said surfactant may be present in the composition in an amount of the order of 0.1 to 8% by weight, preferably 0.5 to 3% by weight, relative to the total weight of the composition;

One or more co-surfactants such as linear fatty alcohols and in particular cetyl and stearyl alcohols;

One or more fatty substances that are liquid at room temperature, commonly known as linear, cyclic or branched, silicone or hydrocarbon-based, volatile or nonvolatile oil(s), for example, silicone oils such as polydimethylsiloxanes (dimethicones), polyalkylcyclo-siloxanes (cyclomethicones) and polyalkylphenyl-siloxanes (phenyldimethicones); synthetic oils such as fluoro oils, alkyl benzoates and branched hydrocarbons such as polyisobutylene; plant oils and especially soybean oil or jojoba oil; and mineral oils such as liquid paraffin; preferably in a proportion of 0.1 to about 10%, better still 0.5 to 5% by weight, relative to the total weight of the composition;

One or more waxes such as ozokerite, polyethylene wax, beeswax or carnauba wax, preferably in a proportion of 0.01 to about 5%, preferably 0.5 to 5% by weight, relative to the total weight of the composition;

One or more silicone elastomers especially obtained by reaction, in the presence of a catalyst, of a polysiloxane having at least one reactive group (especially hydrogen or vinyl) and bearing at least one alkyl (especially methyl) or phenyl end and/or side group, with an organosilicone such as an organohydropolysiloxane, preferably in a proportion of 0.1 to about 20%, preferably 0.25 to 15% by weight, relative to the total weight of the composition;

One or more sunscreens, especially organic screening agents, such as derivatives of dibenzoylmethane (including butyl methoxydibenzoylmethane sold in particular by DSM under the trade name Parsol 1789), derivatives of cinnamic acid (including ethylhexyl methoxycinnamate sold in particular by DSM under the trade name Parsol MCX), salicylates, para-aminobenzoic acids, β-β'-diphenyl acrylates, benzophenones, derivatives of benzylidene camphor, phenylbenz-imidazoles, triazines, phenylbenzotriazoles and anthranilic derivatives; or inorganic screening agents, based on mineral oxides in the form of coated or uncoated pigments or nanopigments, and in particular based on titanium dioxide or zinc oxide; preferably in a proportion of 0.1 to about 30%, better still 0.5 to 20% by weight, relative to the total weight of the composition;

One or more water-soluble dyes such as, for example, disodium salt of ponceau, disodium salt of alizarin green, quinoline yellow, trisodium salt of amaranth, disodium salt of tartrazine, monosodium salt of rhodamine, disodium salt of fuchsin or xanthophyll, preferably in a proportion of 0.1 to about 2% by weight, relative to the total weight of the composition;

One or more fillers, and in particular powders with a soft-focus effect, which may be chosen especially from polyamides, silica, talc, mica and fibers (especially polyamide or cellulose fibers);

One or more preservatives;

sequestrants such as EDTA salts;

fragrances;

and mixtures thereof.

Examples of such adjuvants are especially mentioned in the CTFA Dictionary (International Cosmetic Ingredient Dictionary and Handbook published by The Cosmetic, Toiletry and Fragrance Association, 11th Edition, 2006) which describes a wide variety, without limitation, of cosmetic and pharmaceutical ingredients usually employed in the skin care industry, which are suitable for use as additional ingredients in the compositions according to the present invention.

A person skilled in the art is capable of selecting, from all of these possible additives, both the composition and the amount of these additives that will be added to the composition, in such a way that the latter retains all of its properties.

Moreover, the composition according to the present invention may optionally contain various active agents, which may be selected from the group constituted of vitamins, antioxidants, hydrating agents, emollients, antiaging agents, antipollution agents, keratolytic agents, astringents, nonsteroidal antiinflammatories and bleaching agents.

Examples of vitamins include vitamins A, B1, B2, B6, C and E and their derivatives, pantothenic acid and its derivatives and biotin.

Examples of antioxidants include ascorbic acid and its derivatives such as ascorbyl palmitate, ascorbyl tetraisopalmitate, ascorbyl glucoside, magnesium ascorbyl phosphate, sodium ascorbyl phosphate and ascorbyl sorbate; tocopherol and its derivatives, such as tocopherol acetate, tocopherol sorbate and other esters of tocopherol; BHT and BHA; dibutyl hydroxytoluene, butyl hydroxyanisole, esters of gallic acid, phosphoric acid, citric acid, maleic acid, malonic acid, succinic acid, fumaric acid, cephalin, hexametaphosphate, phytic acid, ethylenediamine-tetraacetic acid and plant extracts, for example from *Chondrus crispus, Rhodiola, Thermus thermophilus*, maté leaf, oak wood, kayu rapat bark, sakura leaves and ylang ylang leaves.

Examples of hydrating agents include polyethylene glycol, propylene glycol, dipropylene glycol, glycerol, 1,3-butylene glycol, xylitol, sorbitol, maltitol, mucopolysaccharides, such as chondroitin sulfuric acid, hyaluronic acid and mucoitin sulfuric acid; caronic acid; atelocollagen; cholesteryl 12-hydroxystearate; biliary salts, a principal component of NHF (natural hydration factor) such as a salt of pyrrolidonecarboxylic acid and a salt of lactic acid, an amino acid analog such as urea, cysteine and serine; a short-chain soluble collagen, diglycerol PPGs, homopolymers and copolymers of 2-methacryloyl-oxyethylphosphorylcholine such as Lipidure HM and Lipidure PBM from NOF; allantoin; PEG/PPG/polybutylene glycol-8/5/3 glycerol from NOF sold under the trade name Wilbride S 753; trimethylglycine sold under the trade name Aminocoat by the company Asahi Kasei Chemicals and various plant extracts such as extracts of Castanea sativa, hydrolyzed hazelnut proteins, Tuberosa polyanthes polysaccharides, Argania spinosa kernel oil and extracts of nacre containing a conchiolin sold notably by the company Maruzen (Japan) under the trade name Pearl Extract®.

Examples of emollients include polyglyceryl methacrylate and methyl gluceth-20.

Examples of anti-aging agents include acylated amino acids (for example Maxilip, Matrixyl 3000 or biopeptide CL from Sederma or Sepilift from SEPPIC), *Pisum sativum* extracts, hydrolyzed soybean proteins, methylsilanol derivatives such as methylsilanol mannuronate, hydrolyzed *Curcubita pepo* meal and *Scenedesmus* extracts.

Examples of antipollution agents include extract of *Moringa pterygosperma* seeds (for example Purisoft from LSN); shea butter extract (for example Detoxyl from Silab), a mixture of ivy extract, phytic acid and sunflower seed extract (for example Osmopur from Sederma).

Examples of keratolytic agents include α-hydroxy acids (for example glycolic, lactic, citric, malic, mandelic or tartaric acids) and β-hydroxy acids (for example salicylic acid), and esters thereof, such as C12-13 alkyl lactates, and plant extracts containing these hydroxy acids, such as *Hibiscus sabdariffa* extracts.

Examples of astringents include *Hamamelis* extracts.

Examples of anti-inflammatory agents include bisabolol, allantoin, tranexamic acid, zinc oxide, sulfur oxide and its derivatives, chondroitin sulfate, glycyrrhizinic acid and its derivatives such as glycyrrhizinates.

Besides the leucodopachrome derivative, the composition according to the invention may comprise an additional bleaching agent capable of blocking the synthesis of structural proteins that are involved in the mechanism of melanogenesis (phase I) such as melanocyte-specific glycoproteins Pme117. Such an active agent may be ferulic acid or Cytovector® (water, glycol, lecithin, ferulic acid, hydroxyethyl cellulose) sold by BASF.

The cosmetic compositions according to the present invention may also contain at least one peptide as described in patent application WO 2009/010356, a bioprecursor as described in patent application WO 2006/134282 or a tranexamate salt such as the hydrochloride salt of cetyl tranexamate.

Besides the leucodopachrome derivative, the composition according to the invention may comprise an additional bleaching agent that has an inhibitory effect on melanin synthesis and/or an inhibitory effect on MITF expression and/or an anti-tyrosinase activity and/or an inhibitory effect on the synthesis of endothelin-1, such as a liquorice extract (*Glycyrrhiza glabra* extract) which is sold in particular by the company Maruzen under the trade name Licorice Extract®.

As a variant or in addition, the composition according to the invention may comprise an additional bleaching agent that also has an antioxidant effect, such as vitamin C compounds, including ascorbate salts, ascorbyl esters of fatty acids or of sorbic acid, and other derivatives of ascorbic acid, for example ascorbyl phosphates, such as magnesium ascorbyl phosphate and sodium ascorbyl phosphate, or saccharide esters of ascorbic acid, which include, for example, ascorbyl 2-glucoside, 2-O-alpha-D-glucopyranosyl L-ascorbate or 6-O-beta-D-galactopyranosyl L-ascorbate. An active agent of this type is sold in particular by the company DKSH under the trade name Ascorbyl Glucoside®.

Other bleaching agents may also be included in the compositions according to the present invention. Mention may be made of depigmenting agents such as plant extracts, including extracts of *Narcissus tazetta*; arbutin, kojic acid, ellagic acid; cysteine; 4-thioresorcin; resorcicol or rucinol or derivatives thereof, glycyrrhizinic acid and hydroquinone-beta-glucoside.

Advantageously, the cosmetic composition according to the invention may be in the form of a powder, an emulsion, a microemulsion, a nanoemulsion, a suspension, a solution, a lotion, a cream, an aqueous or aqueous-alcoholic gel, a foam, a serum, a solution or a dispersion for an aerosol, or a dispersion of lipid vesicles.

In the case of an emulsion, it may be a water-in-oil or oil-in-water emulsion.

In the process according to the invention, the composition may be applied in the morning and/or evening to the skin of the face, décolletage and/or hands, preferably to hyperpigmented areas.

The invention is illustrated nonlimitingly by the examples below.

EXAMPLES

Example 1

Synthesis of a Leucodopachrome Derivative: the Methyl Ester of (S)-triacetyl Leucodopachrome (II)

The compound (II) is obtained from 3,4-dihydroxy-(L)-phenylalanine, hereinafter referred to as (L)-Dopa (V).

The product S-(L)-Dopa methyl ester or methyl ester of (L)-Dopa, referred to as product (VI) is obtained by esterification of the product (L)-Dopa (V), then undergoes an oxidation, then a reduction in order to obtain, after acid hydrolysis, the methyl ester of (S)-5,6-dihydroxyindoline-2-carboxylic acid ((L)-cyclodopa methyl ester or (L)-leucodopachrome methyl ester, product (VII)).

In particular, the S-(L)-Dopa methyl ester (VI) is obtained in the following manner:

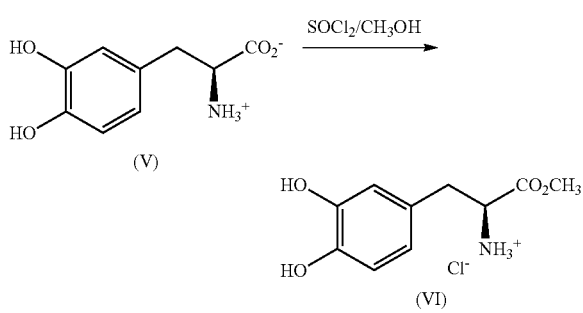

In a round-bottomed flask under a nitrogen atmosphere, 20 ml of anhydrous methanol are cooled to −5° C. using an ice and NaCl bath. Thionyl chloride (5 ml, 14 eq.) is added dropwise.

L-Dopa (V) (1 g, 50 mmol) is added to the reaction medium. The latter is stirred for 1 h at room temperature then brought to reflux for 1 h. The solvent is evaporated.

The ester obtained is a hydrochloride and is in the form of a white solid.

The methyl ester of leucodopachrome (VII) may then be obtained according to the following reaction scheme:

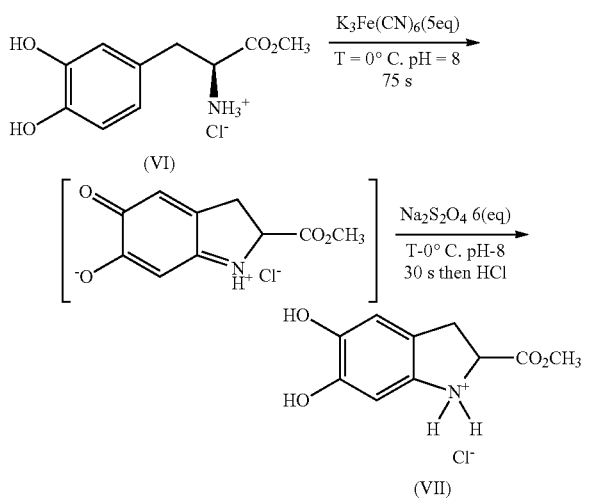

In a round-bottomed flask, S-(L)-Dopa methyl ester (VI) (500 mg, 2.02 mmol, 1 eq.) is dissolved in 150 ml of an aqueous phosphate buffer solution (pH=8, for 1 l of solution: 0.5 g of $KH_2PO_4$ and 22.6 g of $Na_2HPO_4.7H_2O$ are dissolved in distilled water).

The reaction medium is cooled to 0° C. using an ice bath. A solution of $K_3Fe(CN)_6$ (3.325 g, 10.1 mmol, 5 eq.) in 100 ml of phosphate buffer is cooled using the ice bath then added in one go to the reaction medium.

After 75 s, 3.24 g of 85% by weight $Na_2S_2O_4$ (12.4 mmol, 6 eq.) in 50 ml of buffer solution (cooled by the ice bath) are added.

After 30 s, 5 ml of 37% HCl are added. The water is evaporated under reduced pressure. The solid residue is triturated two times with 10 ml of toluene. The toluene phase is concentrated by evaporation of the toluene.

A solid residue of pale brown color is obtained that contains the methyl ester of (S)-leucodopachrome (VII) and the salts of the reaction medium.

The methyl ester of (S)-triacetyl leucodopachrome (II) is then obtained by acetylation of the product (VII):

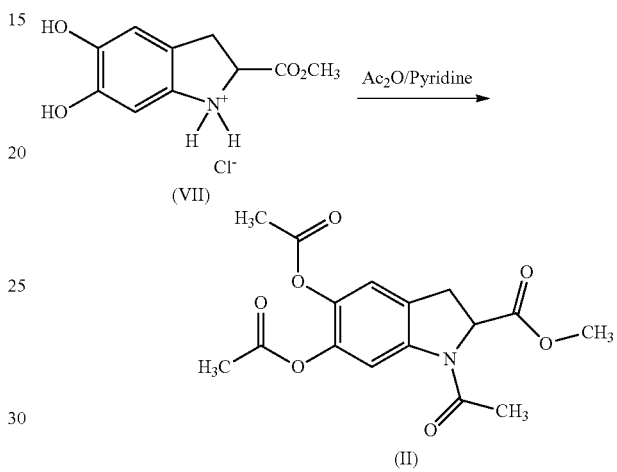

The residue from the preceding step is placed under vacuum then under a nitrogen atmosphere, 25 ml of pyridine and 25 ml of acetic anhydride are added. The reaction medium is triturated in order to break up the solid agglomerates, then stirred for 4 h at room temperature.

The reaction medium is then filtered over celite and washed with 150 ml of dichloromethane before evaporation of the solvent.

Dichloromethane is added to the residue (50 ml) then 50 ml of a 1M solution of HCl. The organic phase is treated with a saturated solution of $NaHCO_3$, with $H_2O$ until neutral pH, then with a saturated solution of NaCl. The organic phase is dried over $MgSO_4$, the solvent is removed by rotary evaporation.

The desired product is obtained in the form of a brown solid with a yield of 77% relative to the S-(L)-Dopa methyl ester (2).

The methyl ester of (S)-triacetyl leucodopachrome (II) is purified over a silica column (dichloromethane/methanol (19/1)).

Example 2

Synthesis of a Leucodopachrome Derivative: the Propyl Ester of (S)-Triacetyl Leucodopachrome (XI)

The compound (XI) is obtained from 3,4-dihydroxy-(L)-phenylalanine, hereinafter referred to as (L)-Dopa (V).

The product S-(L)-Dopa propyl ester or propyl ester of (L)-Dopa, referred to as product (IX) is obtained by esterification of the product (L)-Dopa (V), then undergoes an oxidation, then a reduction in order to obtain, after acid hydrolysis, the propyl ester of (S)-5,6-dihydroxyindoline-2- carboxylic acid ((L)-cyclodopa propyl ester or (L)-leucodopachrome propyl ester, product (X)).

In particular, the S-(L)-Dopa propyl ester (IX) is obtained in the following manner:

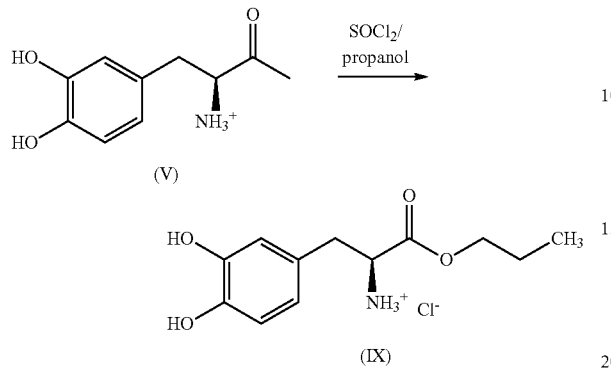

In a round-bottomed flask under a nitrogen atmosphere, 20 ml of anhydrous propanol are cooled to −5° C. using an ice and NaCl bath. Thionyl chloride (5 ml, 2 eq.) is added dropwise.

L-Dopa (V) (1 g, 50 mmol) is added to the reaction medium. The latter is stirred for 1 h at room temperature then brought to reflux for 1 h. The solvent is evaporated.

The ester obtained is a hydrochloride and is in the form of a white solid.

The propyl ester of (S)-leucodopachrome (X) may then be obtained according to the following reaction scheme:

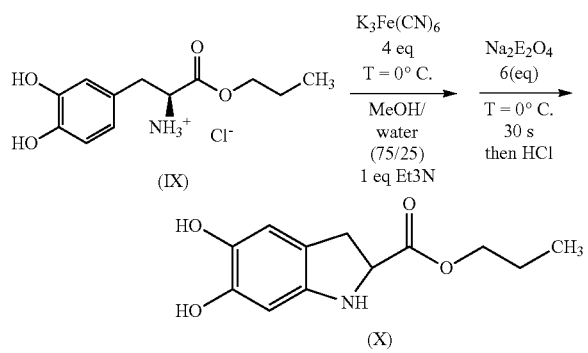

In a round-bottomed flask, S-(L)-Dopa propyl ester (IX) (500 mg, 2.02 mmol, 1 eq.) is dissolved in 150 ml of an MeOH/H$_2$O (75/25) solution with 1 eq. of Et$_3$N (triethylamine).

The reaction medium is cooled to 0° C. using an ice bath. A solution of K$_3$Fe(CN)$_6$ (3.325 g, 10.1 mmol, 4 eq.)

After 75 s, 3.24 g of 85% by weight Na$_2$S$_2$O$_4$ (12.4 mmol, 6 eq.) in 50 ml of MeOH/H$_2$O solution.

After 10 min, 5 ml of 3% HCl are added. The water is evaporated under reduced pressure. The solid residue is triturated two times with 10 ml of toluene. The toluene phase is concentrated by evaporation of the toluene.

A solid residue of pale brown color is obtained that contains the propyl ester of (S)-leucodopachrome (X) and the salts of the reaction medium.

The propyl ester of (S)-triacetyl leucodopachrome (XI) (or methyl ester of triacetyl leucodopachrome) is then obtained by acetylation of the product (X):

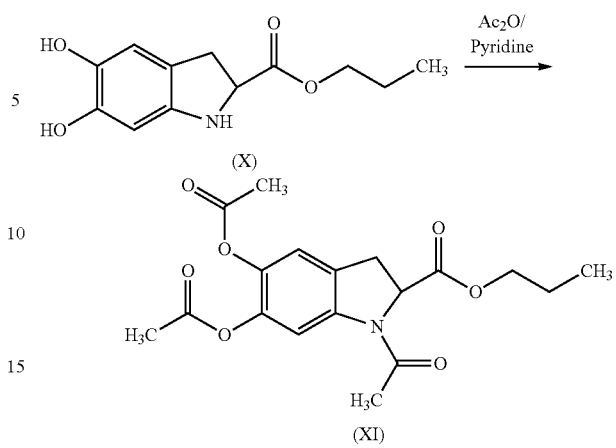

The residue from the preceding step is placed under vacuum then under a nitrogen atmosphere, 25 ml of pyridine and 25 ml of acetic anhydride are added. The reaction medium is triturated in order to break up the solid agglomerates, then stirred for 4 h at room temperature.

The reaction medium is then filtered over celite and washed with 150 ml of dichloromethane before evaporation of the solvent.

Dichloromethane is added to the residue (50 ml) then 50 ml of a 1M solution of HCl. The organic phase is treated with a saturated solution of NaHCO$_3$, with H$_2$O until neutral pH, then with a saturated solution of NaCl. The organic phase is dried over MgSO$_4$, the solvent is removed by rotary evaporation.

The desired product is obtained in the form of a brown solid with a yield of 72% relative to the S-(L)-Dopa propyl ester (IX).

The propyl ester of (S)-triacetyl leucodopachrome (XI) is purified over a silica column (dichloromethane/methanol (19/1)).

Example 3

Oil-in-Water Emulsion

An oil-in-water emulsion having the following composition is prepared:

| Compounds | Trade name | Supplier | CONTENT (in %) |
|---|---|---|---|
| Demineralized water | | | 72.14 |
| Mixture of water, sodium phytate and alcohol | DERMOFEEL PA-3 | LUCAS MEYER | 0.1 |
| Crosslinked acrylate/C10-C30 alkyl acrylate polymer | CARBOPOL ULTREZ 21 | GATEFOSSE | 0.2 |
| Mixture of cetyl alcohol, glycerol stearate, PEG 75 stearate, ceteth-20 and steareth-20 | EMULIUM DELTA | GATEFOSSE | 4 |
| Triheptanoin | DERMOFEEL TC-7 | LUCAS MEYER | 2.5 |
| Squalane | PHYTOSQUALAN | | 3 |
| Tocopheryl acetate | DL-ALPHA-TOCOPHERYL ACETATE | DSM | 0.2 |

-continued

| Compounds | Trade name | Supplier | CONTENT (in %) |
|---|---|---|---|
| Phenoxyethanol | PHENOXY-ETHANOL S | | 0.7 |
| Methyl trimethicone | TMF-1.5 | DKSH | 6 |
| Butylene glycol | 1,3-BUTYLENE GLYCOL | | 4 |
| Methylpropanediol | DUB DIOL | STEARINERIE DUBOIS | 2 |
| Alcohol | 96° EXPORT ALCOHOL | | 5 |
| Compound of formula (I): methyl ester of triacetyl leucodopachrome | | | 0.1 |
| Sodium hydroxide | 25% SODIUM HYDROXIDE SOLUTION | | 0.06 |

The product applied to the skin makes possible a bleaching and a lightening thereof.

Example 4

Aqueous-Alcoholic Gel

An aqueous-alcoholic gel having the following composition is prepared:

| Compounds | Trade name | Supplier | CONTENT (in %) |
|---|---|---|---|
| Demineralized water | | | 83.55 |
| Mixture of water, sodium phytate and alcohol | DERMOFEEL PA-3 | LUCAS MEYER | 0.1 |
| Mixture of sorbeth-30 tetraisostearate, sorbitan sesquistearate, PPG-8-Ceteth-20, acrylate/beheneth-20 methacrylate copolymer, dipropylene glycol and water | NIKKOMULESE SE | GATEFOSSE | 4.5 |
| Phenoxyethanol | PHENOXY-ETHANOL S | COGNIS CORP | 0.7 |
| Butylene glycol | 1,3-BUTYLENE GLYCOL | | 4 |
| Methylpropanediol | DUB DIOL | STEARINERIE DUBOIS | 2 |
| Alcohol | 96° EXPORT ALCOHOL | | 5 |
| Compound of formula (I): methyl ester of triacetyl leucodopachrome | | | 0.1 |
| Potassium hydroxide | 85-8 PURE POTASSIUM HYDROXIDE PELLET | | 0.05 |

The gel applied to the skin makes possible a bleaching and a lightening thereof.

Example 5

Effect of the Methyl Ester of Triacetyl Leucodopachrome on Melanin Synthesis 3 solutions of methyl ester of triacetyl leucodopachrome were prepared, respectively at concentrations of 0.0025%, 0.00025% and 0.000025% by weight in DMSO.

The effect of the methyl ester of (S)-triacetyl leucodopachrome on melanin synthesis was evaluated according to the following procedure.

Hyperpigmented melanocytes derived from normal neonatal prepuce of separate donors were bought from the company Cascade Biologics (Portland, Oreg., United States). The cells were seeded in 6-well plates and cultured in a growth medium of the melanocytes (medium topped up with bovine pituitary extract, fetal bovine serum, bovine insulin, transferrin, conventional fibroblast growth factor, hydrocortisone, heparin and phorbol 12-myristate 13-acetate).

In a second stage, the cells were incubated with a growth medium (MGM, Clonetics) containing the active products, in three copies, for 5 days. The medium was withdrawn and the cells washed with PBS (Gibco/Invitrogen). The cells were lyzed and the melanin solubilized in NaOH.

The supernatant was centrifuged. After centrifugation, the clear lysate was transferred to a new plate and the melanin content was measured on an ELISA reader at 490 nm. The pellets were visualized on an AlphaInnotech imager.

The results were the following:

| Content of methyl ester of (S)-triacetyl leucodopachrome | % inhibition of melanin synthesis |
|---|---|
| 0.0025% | 32.76 |
| 0.00025% | 6.70 |
| 0.000025% | 5.49 |

An inhibition of the melanin synthesis is observed, which increases with the concentration of methyl ester of (S)-triacetyl leucodopachrome in the solution.

The invention claimed is:

1. A cosmetic or dermatological topical composition, comprising, in a physiologically acceptable medium, at least one compound of formula (I)

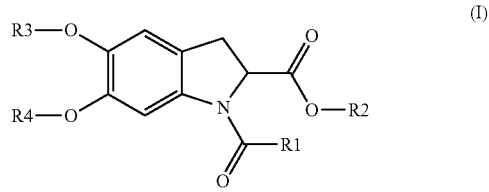

where R1 is:
saturated or unsaturated, linear or branched C1-C18 alkyl, optionally substituted with one or more aryl groups;
R2 is:
saturated or unsaturated, linear or branched C1-C18 alkyl, or
a polyethylene glycol (PEG) chain or a polyethylene glycol monoalkyl ether chain; and R3 and R4 are, independently of one another:
an acyl group of formula R5-CO— where R5 is a saturated or unsaturated, linear or branched C1-C18 alkyl, optionally substituted with one or more aryl groups that are optionally substituted with acyloxy groups.

2. The composition as claimed in claim 1, wherein R2 is a polyethylene glycol (PEG) chain.

3. The composition as claimed in claim 1, wherein R1 is —CH$_3$ and R2 is —CH$_3$ or —CH$_2$—CH$_3$.

4. The composition as claimed in claim 1, wherein R3 and R4 are both CH$_3$—CO— acetyl groups.

5. The composition as claimed in claim 1, wherein the at least one compound of formula (I) is the methyl ester of triacetyl leucodopachrome (II) or the ethyl ester of triacetyl leucodopachrome (III):

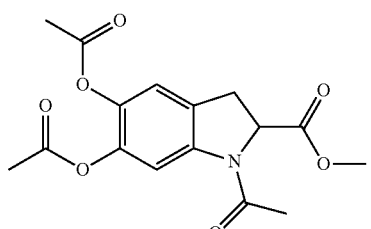
(II)

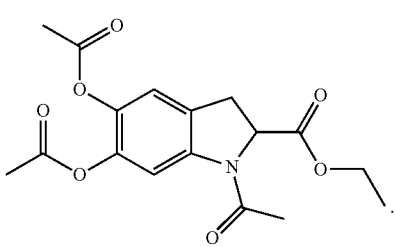
(III)

6. The composition as claimed in claim 1, wherein the at least one compound of formula (I) is one of the enantiomers or a racemic (50/50) mixture of two optically active compounds of formula (I).

7. The composition as claimed in claim 1, wherein the at least one compound of formula (I) is present in an amount ranging from 0.00001 to 10% by weight relative to the total weight of the composition.

8. A process for reducing pigmentation and/or bleaching and/or lightening the skin, comprising applying to the skin of a cosmetic or dermatological topical composition, wherein the composition comprises, in a physiologically acceptable medium, at least one compound of formula (I)

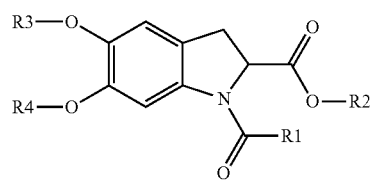
(I)

where R1 is:
saturated or unsaturated, linear or branched C1-C18 alkyl, optionally substituted with one or more aryl groups;

R2 is:
saturated or unsaturated, linear or branched C1-C18 alkyl, or
a polyethylene glycol (PEG) chain or a polyethylene glycol monoalkyl ether chain; and R3 and R4 are, independently of one another:
an acyl group of formula R5-CO— where R5 is saturated or unsaturated, linear or branched C1-C18 alkyl, optionally substituted with one or more aryl groups that are optionally substituted with acyloxy groups;
said composition being as claimed in claim 1.

9. The process as claimed in claim 8, wherein the composition inhibits the synthesis of melanin.

10. A compound of formula (I')

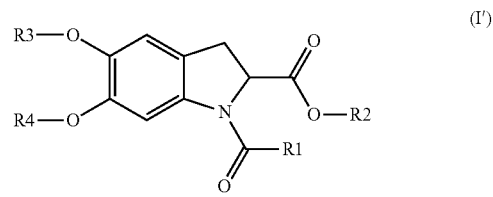
(I')

where R1 is:
saturated or unsaturated, linear or branched C1-C18 alkyl, optionally substituted with one or more aryl groups;

R2 is:
saturated or unsaturated, linear or branched C3-C18 alkyl, or
a polyethylene glycol (PEG) chain or a polyethylene glycol monoalkyl ether chain; and R3 and R4 are, independently of one another:
an acyl group of formula R5-CO— where R5 is saturated or unsaturated, linear or branched C1-C18 alkyl, optionally substituted with one or more aryl groups that are optionally substituted with acyloxy groups.

11. The compound as claimed in claim 10, wherein R2 is:
a linear C3-C18 alkyl group, or
a polyethylene glycol (PEG) chain or a polyethylene glycol monoalkyl ether chain.

12. The compound as claimed in claim 10, wherein the compound of formula (I') is the propyl ester of triacetyl leucodopachrome of formula (IV)

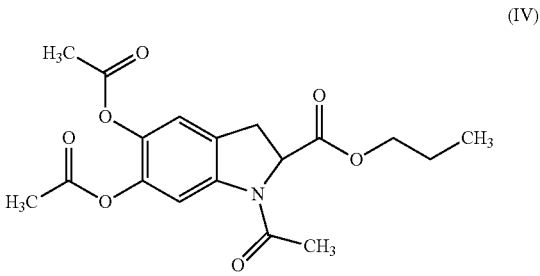 [SMILES: CCCOC(=O)C1Cc2cc(OC(C)=O)c(OC(C)=O)cc2N1C(C)=O]
(IV)

optionally in the form of one of the enantiomers or a racemic (50/50) mixture of two optically active compounds of formula (IV).

13. The composition as claimed in claim 7, wherein the at least one compound of formula (I) is present in an amount ranging from 0.001 to 5% by weight relative to the total weight of the composition.

* * * * *